United States Patent [19]
Lipskier

[11] Patent Number: 5,910,286
[45] Date of Patent: Jun. 8, 1999

[54] HIGHLY SELECTIVE CHEMICAL SENSOR

[75] Inventor: Jean-François Lipskier, Verrieres Le Buisson, France

[73] Assignee: Thomson-CSF, Paris, France

[21] Appl. No.: 08/722,147

[22] PCT Filed: Feb. 20, 1996

[86] PCT No.: PCT/FR96/00267

§ 371 Date: Oct. 17, 1996

§ 102(e) Date: Oct. 17, 1996

[87] PCT Pub. No.: WO96/26435

PCT Pub. Date: Aug. 29, 1996

[30] Foreign Application Priority Data

Feb. 21, 1995 [FR] France .................................. 95 01971

[51] Int. Cl.$^6$ .......................... G01N 15/06; G01N 33/00; G01N 33/48
[52] U.S. Cl. ............................................................ 422/68.1
[58] Field of Search ............................................. 422/68.1

[56] References Cited

U.S. PATENT DOCUMENTS

| | | | |
|---|---|---|---|
| 5,151,110 | 9/1992 | Bein et al. | ................................... 55/75 |
| 5,325,704 | 7/1994 | Mariani et al. | ........................ 73/24.06 |

OTHER PUBLICATIONS

Dario Kriz, et al., "Preparation and Characterization of Composite Polymers Exhibiting . . . ", 1995 81–90.

D. Kriz, et al., Analytica Chimica Acta 300, (1995) 71–75, Competitive Amperometric Morphine Sensor Based on an Agarose Immobilised Molecularyly Imprinted Polymer.

S.A. Piletsky, et al., Sensors and ActuatorsB, 18–19, (1994), 629–631, Sensors for Low–Weight Organic Molecules Based on Molecular Inprinting Technique.

S.A. Piletsky, et al., Institute of Bioorganic Chemistry and Oil Chemistry and Oil Chemistry, Ukrainian SSR, Kiev, (1990), 55–58, "Substrate–Selective Polymeric Membranes, Selective Transfer of Nucleic Acids Components".

D. Kriz, et al., Anal. Chem. (1995), 67, 2132–2144, "Introducing Biomimetic Sensors Based on Molecularly Imprinted Polymers as Recognition Elements".

*Primary Examiner*—Avis M. Davenport
*Attorney, Agent, or Firm*—Oblon, Spivak, McClelland, Maier & Neustadt, P.C.

[57] ABSTRACT

The invention relates to a highly selective chemical sensor comprising an acoustic wave transducer and a sensitive layer of so-called "molecular fingerprint" material. This is a macroporous crosslinked material having cavities whose steric and functional configuration is specifically suited to capturing molecular and/or ionic species.

18 Claims, 6 Drawing Sheets

HIGHLY SELECTIVE CHEMICAL SENSOR

The field of the invention is that of chemical sensors and more particularly that of highly selective chemical sensors which are capable of reporting the presence of a particular chemical species (also known as analyte) in a given medium.

In general, a chemical sensor consists of a sensitive layer, capable of binding the analyte more or less reversibly and selectively and of a transducer whose role is to convert the variation of a physicochemical parameter during the binding of the analyte into a signal which is generally electrical. The sensitivity of the sensor is defined by the lower limit of detection, that is to say the minimum amount or concentration of analyte which induces an identifiable signal relative to the noise. The selectivity of the sensor corresponds to its capacity to distinguish the analyte from the other chemical species which may be present in the medium. A very selective sensor is thus characterized in that at identical concentrations, the signal induced by the presence of the analyte is much more intense than the signal induced by any other chemical species. One of the main difficulties encountered in this field is to prepare sensors which are both sensitive and highly selective. Such chemical sensors may be applied in particular to the qualitative and quantitative detection of pollutants and toxic agents, or alternatively to process control in the chemical or pharmaceutical industry, to biological diagnosis, etc.

Currently, chemical sensors exist that are extremely selective by virtue of a sensitive layer containing molecules of biological origin such as proteins (enzymes, antibodies), nucleic acids (DNA or RNA) or even whole microorganisms. The main drawback of such sensors lies in their excessive fragility which seriously limits the operating and storage conditions of these sensors and which greatly reduces their lifetime. Moreover, the development and production costs of such sensors are generally very high.

In parallel with biological molecules, there are also less fragile synthetic organic molecules which can be used in the sensitive layer. These molecules are, in particular, crown ethers, cryptands, carcerands, spherands, polycyclophanes or cyclodextrins. The three-dimensional structure of these molecules generally has a cavity. The size and electron density distribution of this cavity are such that a particular chemical species which is included therein can find itself stabilized relative to the external medium. The synthesis of these "host" molecules is, however, particularly complex, and of very low yield. Moreover, it is not always possible to construct a cavity suited to recognition of the desired analyte. Lastly, these molecules cannot be used directly, but must be either chemically attached to the surface of the transducer or incorporated into a polymer matrix which is permeable to the analyte. This usually involves an additional functional-group installation, and thus further synthetic steps.

In this context, the invention proposes to use recently-developed materials known as "molecular fingerprints" having a selective "memory" for the molecules which have been used, in order to construct the architecture for them with very specific sites. These are materials obtained according to the following principle:

in a first stage, the incubation of molecular or ionic species G' which serve as a gauge in the presence of polymerizable monomers and crosslinking agents is carried out in order to arrive at the development of complementary interactions;

in a second stage, the above mixture is polymerized around the monomers-gauge complex;

lastly, the species G' are extracted.

After this last step, a crosslinked macroporous material is obtained having cavities whose steric and functional configuration is perfectly suited for the subsequent binding of new molecules G that are identical or very similar to the species G', with an affinity and a selectivity which are close to those offered by biological systems.

More precisely, the invention relates to a chemical sensor using such materials and detection by acoustic waves whose propagation may be affected in a medium or at the surface of a medium when the latter changes, and more particularly, in the present case, when the so-called "molecular fingerprint" material has trapped molecules of type G.

The subject of the invention is thus a chemical sensor which is selective for a species G, comprising an acoustic wave transducer and a sensitive layer, characterized in that the sensitive layer consists of a crosslinked, macroporous material having cavities whose steric and functional configuration is specifically suited to capturing a species G, in the cavities.

The crosslinked macroporous material is preferably a highly crosslinked organic polymer obtained by polymerization of a composition comprising one or more monomers that are crosslinkable in the presence of species G or G' (similar to G), of molecular and/or ionic type, or a combination of molecules and/or ions of given stoichiometry.

The transducer of the chemical sensor according to the invention may advantageously be a volume wave transducer, comprising a piezoelectric material inserted between two electrodes, at least one of the electrodes being coated with the sensitive layer.

The transducer of the chemical sensor according to the invention may also advantageously be a surface wave transducer.

In this case, the transducer may comprise a piezoelectric material on which two interlocked series of electrodes are placed, separated by a surface, the sensitive layer being placed on the surface.

In order to promote adhesion of the sensitive layer to the surface of the piezoelectric material or to the surface of an electrode (in the case of a volume wave transducer), the said surface may be coated beforehand with a layer L2 which allows specific bonds to be created at the sensitive layer/support layer interface.

The subject of the invention is also a process for the preparation of a combination of chemical sensors, characterized in that it includes, at the surface of a substrate (S) which allows the propagation of acoustic waves:

the preparation, through the agency of a first mask which leaves a first area (A1) of the substrate free, of a first component of the molecular fingerprint material (I);

the preparation, through the agency of a second mask which leaves the second area (A2) of the substrate free, of a second material component (II) which is crosslinked in the absence of gauge molecule;

the preparation, on either side of each area (A1, A2), of acoustic wave inducer and/or receptor means.

In a variant of the process according to the invention, the latter includes the following steps:

a) preparation on a substrate (S) which allows the propagation of acoustic waves with alternation of a first layer of resin (R1) for photolithography, of a metal layer (M1) and of a second layer of resin (R2) for photolithography;

b) elimination of the second layer of resin in a first area (A1);

c) etching of the metal layer in a first area (A1);

d) attack of the first layer of resin in the first area (A1) and possibly of the rest of the second layer of resin;

e) exposure of the substrate in the first area during attack of the first layer of resin;

f) preparation, on the substrate in the first area, of a first component (I) made of molecular fingerprint material;

f) preparation of a third layer of resin (R3);

h) elimination of the third layer of resin (R3) in a second area (A2);

i) etching of the metal layer in the second area (A2);

j) attack of the first layer of resin in the second area and possibly of the rest of the third layer of resin;

k) exposure of the substrate in the second area during attack of the first layer of resin;

l) preparation, on the substrate in the second area, of a second component (II) made of material crosslinked in the absence of gauge molecule;

m) elimination of the metal layer (M1) and of the first layer of resin (R1).

The second component (II) may advantageously be made of material identical in composition to that of the first component (I), but it is polymerized and crosslinked in the absence of gauge molecule.

The invention will be better understood and other advantages will emerge on reading the description which follows, given without any limitation being implied, and by means of the attached figures among which:

Figure 5A:
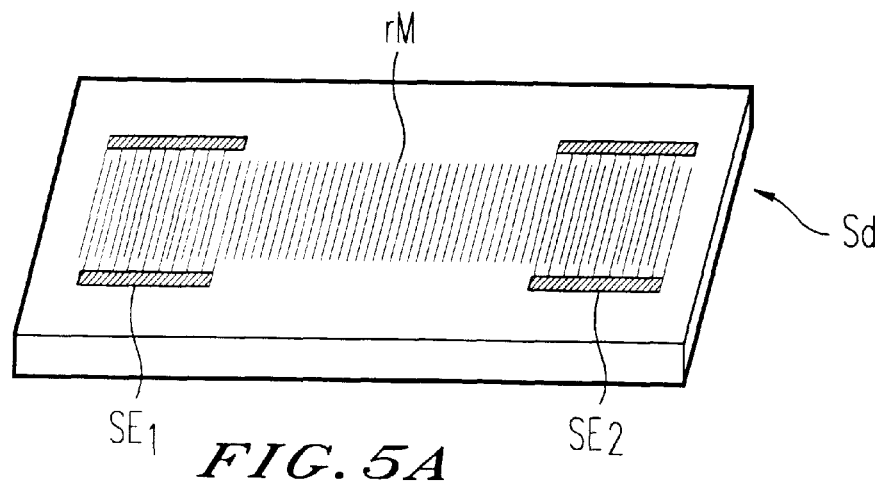
FIG. 5 illustrates an example of a sensor according to the invention in which acoustic waves of Love wave type are obtained by means of the presence of a network structure.
Figure 5B:
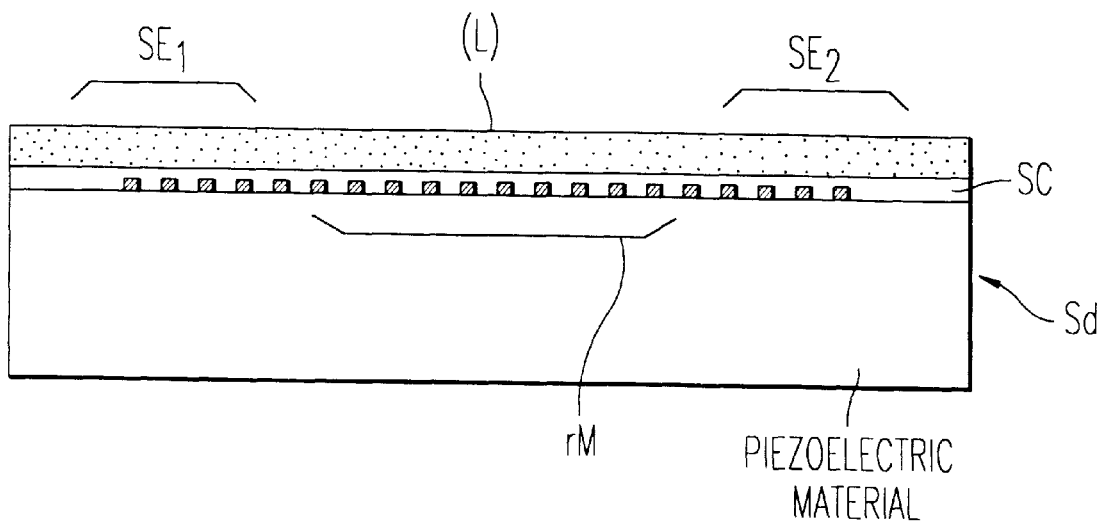
Figure 6:
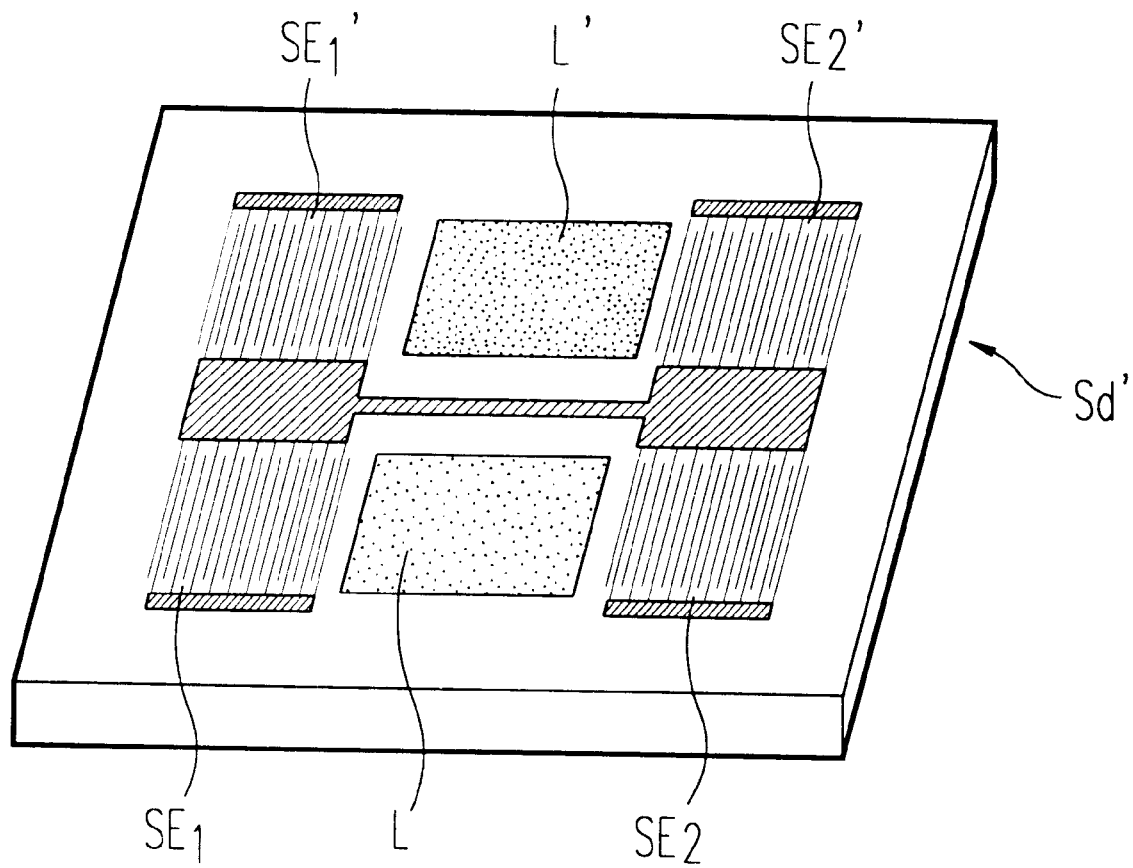
Figure 7A:
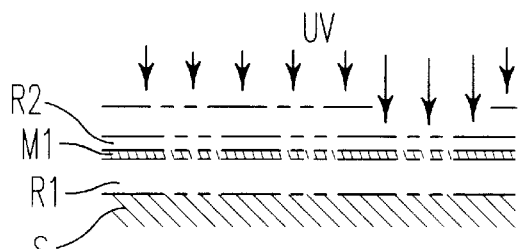
Figure 7B:
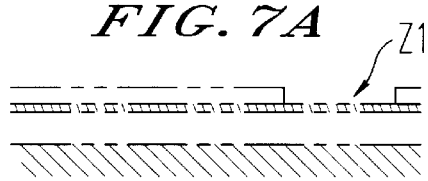
Figure 7C:
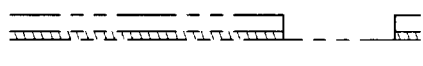
Figure 7D:
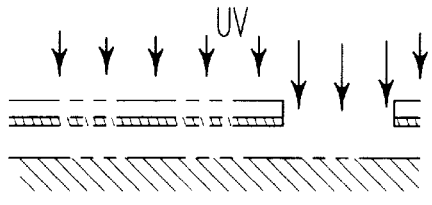
Figure 7E:
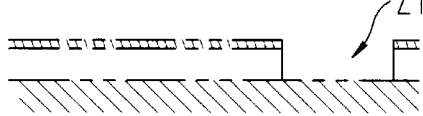
Figure 7F:
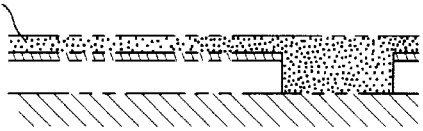
Figure 7G:
Figure 7H:
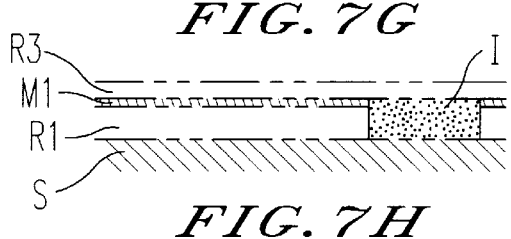
Figure 7I:
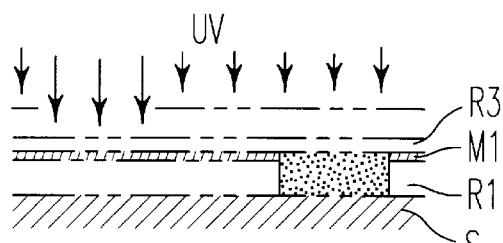
Figure 7J:
Figure 7K:
Figure 7L:
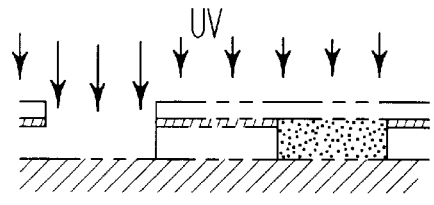
Figure 7M:
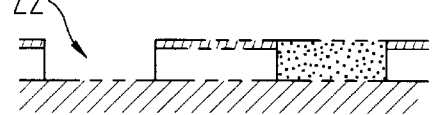
Figure 7N:
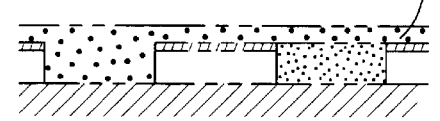
Figure 7O:
Figure 7P:
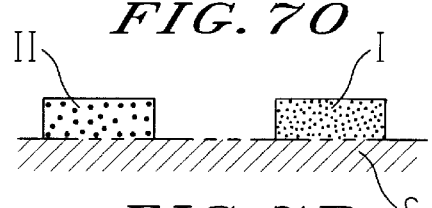

FIG. 5a schematically represents the network rm and the series of electrodes $SE_1$ and $SE_2$;

FIG. 5b schematically represents a section of this sensor;

FIG. 6 schematically represents the combination of two identical transducers, only one of which can trap species G;

FIG. 7 illustrates an example of a production process which makes it possible to obtain the combination described in FIG. 6.

The chemical sensor according to the invention results from the combination of a sensitive layer of molecular fingerprint materials and an acoustic wave transducer. These materials have the advantage of having very good mechanical, thermal and chemical stability and of being particularly easy and inexpensive to implement when compared with the materials used in biosensors. Thus, they can be used over a wide temperature range and have the great advantage of being able to be used equally in aqueous and organic phase, or alternatively in ambient air.

The combination of a molecular fingerprint material and an acoustic transducer makes it possible to develop a particularly sensitive sensor insofar as a variation in mass (capture or otherwise of molecules) necessarily induces a variation in the propagation of the acoustic waves, whereas certain physical properties may not be modified (electrochemical properties, light polarization, etc.). Moreover, acoustic wave devices are generally robust, sensitive and inexpensive.

Figure 1:
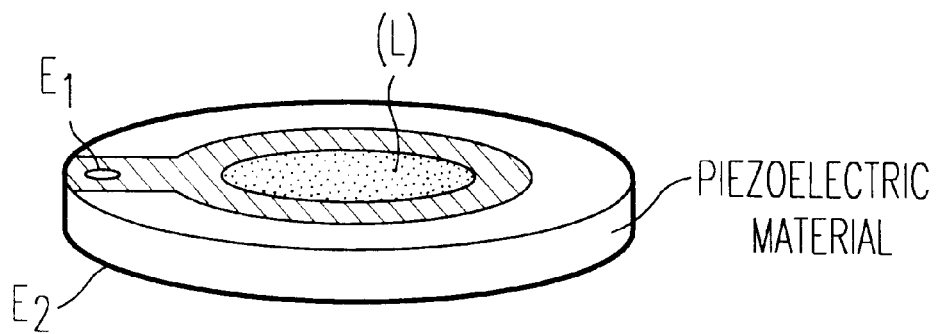
FIG. 1 illustrates an example of a sensor according to the invention, using a volume wave transducer.

In a first variant of the invention, the chemical sensor comprises a volume wave transducer consisting of piezoelectric material; this can be a plate made of quartz, or of any other piezoelectric material, fitted with two electrodes E1 and E2, as illustrated in FIG. 1. The molecular fingerprint material L is arranged on one of the electrodes, or even on both of them. The device thus developed constitutes a resonator whose frequency may be measured. The absorption or adsorption of the molecules which it is desired to detect selectively, within the host material, is reflected by an increase in mass Δm and leads to a variation in resonance frequency of the resonator thus made.

This frequency variation is given in a first approximation by the Sauerbrey equation below:

$$\Delta F = -2F^2 \Delta m / \rho_q v_q A$$

with F the frequency of the resonator (Hz) $\rho_q$ the density of the piezoelectric material $v_q$ the speed of propagation of the acoustic waves (m/s) A the area of the sensitive surface (m$^2$)

Figure 2A:
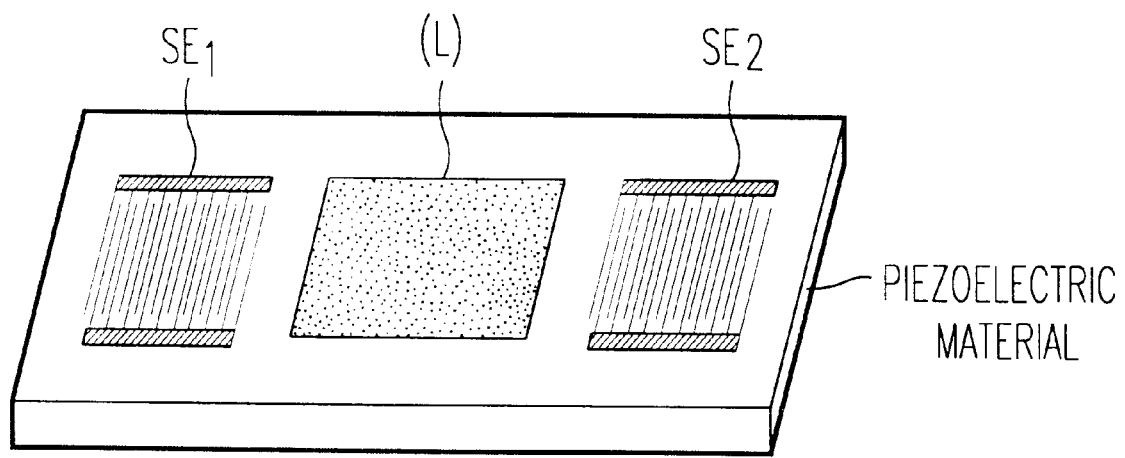
FIG. 2a illustrates an example of a sensor according to the invention using a surface wave transducer, of Rayleigh wave type.

In a second variant of the invention as illustrated in FIG. 2a, the chemical sensor comprises a surface wave transducer consisting of a piezoelectric material, on which are placed two interlocking series of electrodes $SE_1$, and $SE_2$, between which is deposited the layer of sensitive molecular fingerprint material L.

Figure 2B:
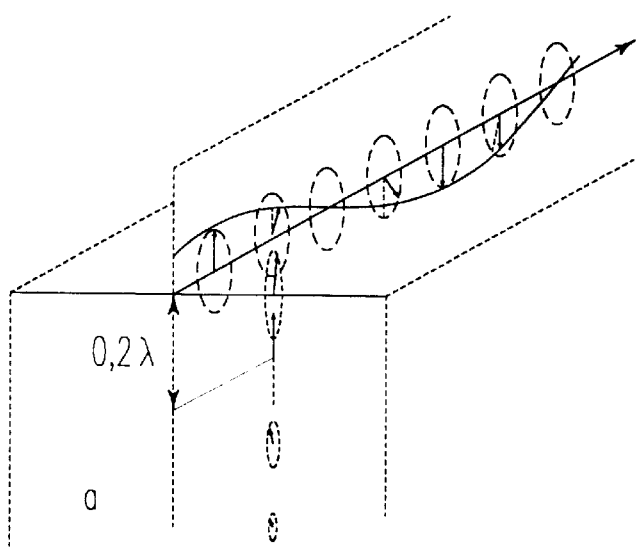
FIG. 2b illustrates the propagation of the Rayleigh waves.

The assembly constitutes a delay line, the acoustic waves emitted by the first series of electrodes $SE_1$ propagate up to the second series of electrodes $SE_2$ with a certain delay, reflected by a phase variation. By recombining the output signal and the input signal, the output signal being amplified and placed in phase with the input signal, an oscillating circuit having a characteristic resonance frequency $f_1$ is produced. When the conditions of propagation of the surface acoustic waves are modified between the two series of electrodes, the phase variation induced is no longer the same, and the oscillating circuit no longer resonates at the same frequency $f_1$, but then resonates at the frequency $f'_1$. FIG. 2b illustrates the propagation of Rayleigh waves of wavelength $\lambda$.

In the sensor according to the invention, analysis of the variation in frequency makes it possible to monitor the capture of molecules by the sensitive layer. The reason for this is that this capture is reflected by a variation in mass which gives rise to a modification of the propagation of the surface acoustic waves.

It should be noted that Rayleigh waves, which propagate at the surface of a piezoelectric medium, are dampened in liquid media. Thus, when a surface wave chemical sensor of Rayleigh wave type is used in solution, it is desirable to proceed in several stages:

in a first stage, the resonance frequency of the oscillator is determined in dry conditions;

the sensor is then placed in equilibrium with the solution to be analysed;

the sensor is extracted and rinsed with a small amount of pure solvent in order to eliminate the molecules adsorbed non-specifically;

the sensor is dried under a jet of inert gas;

the resulting variation in frequency is measured.

The chemical sensor according to the invention may advantageously comprise a surface wave transducer of Lamb wave type, which waves are generated by the presence of a low thickness of piezoelectric material. The sensitive layer can be deposited at the surface of the thin film of piezoelectric material on the side of the series of electrodes or alternatively on the opposite side to the series of electrodes. The latter variant has the advantage of making it possible to encapsulate the whole device so that only the molecular fingerprint material is in contact with the medium to be analysed. Thus, the metal electrodes, the piezoelectric material and any associated electronics are protected against chemical attack which may occur on contact with this medium.

Figure 3:
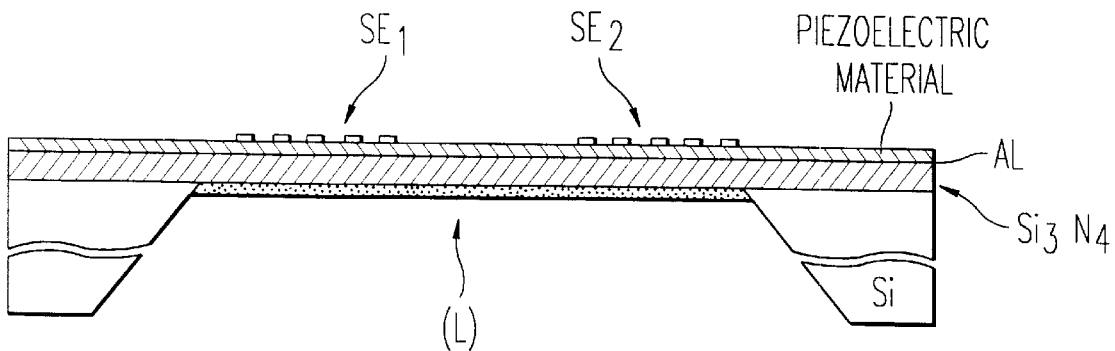
FIG. 3 illustrates another example of a sensor according to the invention, using a surface wave transducer, of Lamb wave type.

FIG. 3 illustrates an example of a device obtained by anisotropic etching on the rear face of a silicon substrate on which are deposited beforehand a silicon nitride attack-protective layer and a layer of zinc oxide piezoelectric material or aluminium nitride piezoelectric material, separated by an aluminium film. The thickness of the membrane thus produced is about 3 μm indicates the layer of the sensitive material and $SE_1$ and $SE_2$ indicate the electrodes.

Figure 4A:
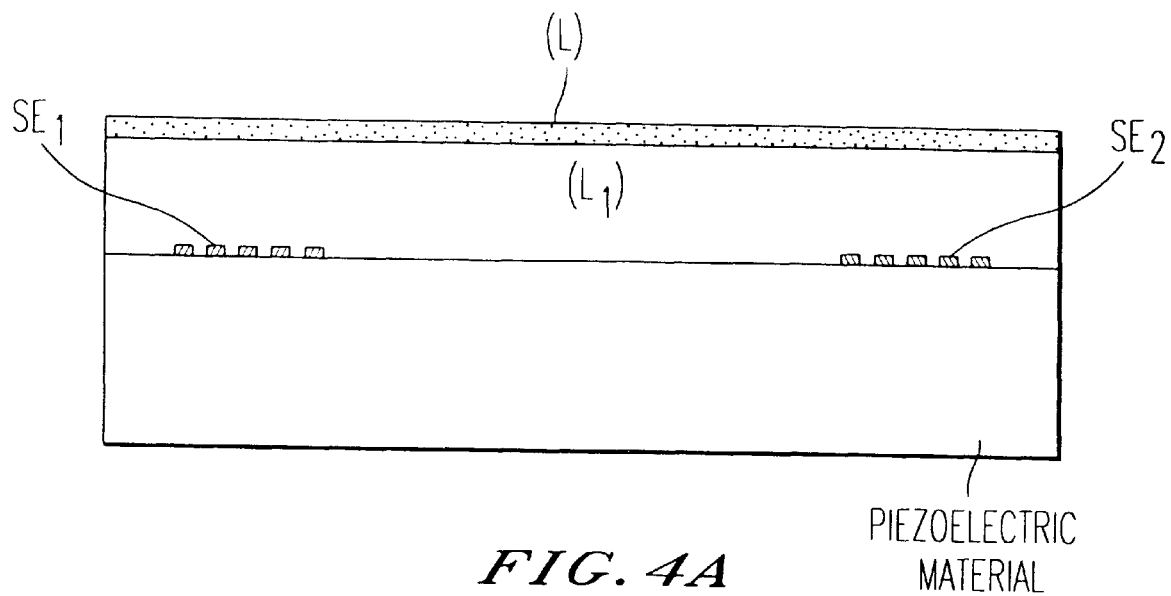
FIG. 4a illustrates an example of a sensor according to the invention using a surface wave transducer, of Love wave type.
Figure 4B:
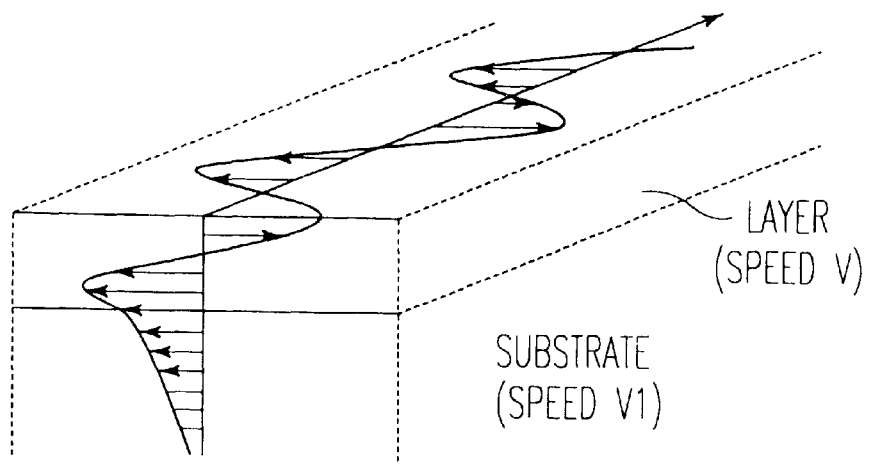
FIG. 4b illustrates the propagation of Love waves in the intermediate layer.

According to another variant of the invention, the chemical sensor comprises a surface acoustic wave transducer of Love wave type, which propagates in an intermediate material (layer L1) located between the piezoelectric material and the sensitive layer (L); in this intermediate material the speed of propagation of the acoustic waves (speed V) is lower than that (speed V1) of the acoustic waves in the piezoelectric material. This intermediate layer may typically be made of silica, gold, aluminium (Stevenson, A.C.; Gizeli, F; Goddard, N.J. and Lowe C.R., Sens. Actuators B., 13–14 (1993), 636–637) (FIG. 4a and FIG. 4b). $SE_1$ and $SE_2$ represents the electrodes.

The intermediate layer may be replaced by a metallic network structure used to confine the acoustic wave to the surface of the piezoelectric material. Such a device sd is represented schematically in FIGS. 5a and 5b. In this case, a very fine layer of silica (sc) may be deposited on the piezoelectric material on which the two interlocking series of electrodes ($SE_1$, $SE_2$) and the network structure (rm) have previously been produced. This layer of silica may be obtained by spraying or by plasma-assisted vapour phase chemical deposition, and its function is to promote the adhesion of the sensitive layer (L).

In order to get rid of spurious effects associated, for example, with temperature fluctuations, it is generally advantageous to combine two identical transducer devices, only one of which is coated with a sensitive layer, and to carry out a differential measurement. In the present case, an additional advantage may be obtained, according to FIG. 6, by carrying out a differential measurement on two transducers that are identical except for the fact that one is coated with a molecular fingerprint material (material I) and the other is coated with a material of identical composition, polymerized and crosslinked in the absence of gauge molecule (material II). The reason for this is that a molecular fingerprint material can have, besides the binding sites specifically suited to the analyte to be detected, non-specific sites which can bind other molecules. On the other hand, the material II possesses only non-specific sites. It is thus possible to subtract the interference which may be due to molecules other than the analyte, which become bound to the sensitive layer by non-specific interactions.

Lastly, there may be an advantage in combining several transducers coated with various molecular fingerprint materials so as to make a system suited to the detection and quantification of a plurality of different analytes.

In general, the molecular fingerprint materials are preferably used in the form of films. These films may advantageously be produced by in-situ polymerization, from a liquid mixture comprising the molecule which serves as a gauge (G'), one (or more) polymerizable or polycondensable functional monomer(s) (M), one or more crosslinking agent(s) R and one (or more) polymerization initiator(s) (A), these various components optionally being dispersed in a solvent. The said mixture may then be deposited by centrifugation or by any means capable of obtaining, after evaporation of any possible solvent, a uniform deposition of the reagents. The polymerization may be carried out thermally or, better still, photochemically. The latter approach offers the advantage of being faster, and of being able to be carried out at moderate temperatures, which limits the risks of degradation of the gauge molecule.

The molecule (G) which serves as a gauge may typically be an ion, an organic molecule of biological or synthetic origin, a polypeptide, a polynucleotide, a polysaccharide or any other chemical species which may be of value in detecting selectively.

The functional monomers (M) are preferably molecules containing at least one fragment capable of undergoing a polymerization or polycondensation reaction, and at least one fragment capable of establishing a hydrogen bond, an ionic bond, a coordination bond, a reversible covalent bond or any other type of reversible bond of sufficient energy, with the gauge molecule. Acrylic acid, methacrylic acid, itaconic acid, 2-acrylamido-2-methyl-1-propanesulphonic acid, N-vinylpyrrolidone, 2-hydroxyethyl acrylate, 2-hydroxypropyl acrylate, 1-aza-5-hydroxymethyl-3,7-dioxabicyclo(3.3.0)octane acrylate, vinylpyridines, vinylacetic acid, and 4-vinylphenylboronic acid are examples of such functional monomers.

The crosslinking agents (R) are preferably molecules having at least two polymerizable or polycondensable groups that are compatible with the functional monomers. Ethylene glycol diacrylate or dimethacrylate, 1,4-butanediol diacrylate, 1,2-bis(N,N'-acrylamido)ethane, 1,4-divinylbenzene, trimethylolpropane (2-ethyl-2-hydroxymethyl-1,3-propanediol) triacrylate or trimethacrylate, and pentaerythritol triacrylate are examples of crosslinking agents given without any limitation being implied.

The polymerization initiator is a chemical species capable of forming one or more active secondary species, either thermally or under the influence of radiation. Such initiators are well known to those skilled in the art. Examples which may be mentioned are:

radical polymerization initiators such as azo-bis nitriles, substituted acetophenones, benzoins, benzoyl oximes, phosphine oxides and peresters;

cationic polymerization initiators such as aryldiazonium salts or onium salts, thiapyrilium derivatives and ferrocenium salts.

In order to enhance the adhesion of the molecular fingerprint material, the surface of the transducer may advantageously be functionalized prior to the deposition, the aim of this operation being to allow, or to promote, the establishment of covalent bonds between the atoms at the surface of the transducer and the molecules of the coating. When the surface to be functionalized consists of silica, silicon nitride or oxynitride, lithium niobate, aluminium oxide, titanium, zirconium, silanes of general formula $R_nSiX_{(n-4)}$, where X is a hydrolysable group (typically an alkoxy, acyloxy or amine group or a chlorine atom) and R is a non-hydrolysable organic group having a function capable of reacting with monomers M, may be used as coupling agents. By way of example, if the polymer to be deposited is based on acrylic monomers, 3-N-(3-acryloxy-2-hydroxypropyl)-aminopropyltriethoxysilane, 3-methacryloxytrimethoxypropylsilane or 3-methacryloxytriethoxypropylsilane may be used. A gold surface may be functionalized using coupling agents of RSH or RS-SR' type where R and R' are non-hydrolysable organic groups having, if necessary, a function capable of reacting with the monomers M. 2-Methacryloyloxyethyl methyl disulphide is an example of an agent of RS-SR' type having a non-hydrolysable organic group which can be polymerized in the presence of monomers M of acrylic type. 11-Hydroxyundecanethiol is an example of an agent of RSH type where R is a non-hydrolysable and non-polymerizable organic group; this agent is known to promote the adhesion of acrylic polymers to a gold surface (Konstadinidis, K.;Evans, J.F.; Tirrell, M. and Nuzzo, R., Polym. Prepr. 31 (2), 525–6 (1990)).

EXAMPLE 1

A volume acoustic wave transducer is prepared from a cylindrical AT quartz crystal 16 mm in diameter. A gold electrode 9 mm in diameter is deposited by spraying onto each of the bases of the cylinder, so as to produce a resonator oscillating at 6 Mhz. The assembly is immersed for 24 h in a 1 mM solution of 2-methacryloyloxyethyl methyl disulphide (prepared according to the method described by Ederlen et al. (Ederlen, C.; Haussling, L.; Naumann, R.; Ringsdorf, H.; Wolf, H.; Ynag, J. Langmuir (1994)), 10, 1246–1250) in chloroform and is then rinsed with chloroform and dried. One drop of a solution typically comprising 5 mmol of atrazine, 10 mmol of N,N-dimethylaminoethyl methacrylate, 10 mmol of methacrylic acid, 60 mmol of ethylene glycol dimethacrylate and 140 mg of 2,2'-azobis (2,4-dimethylvaleronitrile) in 15 ml of distilled chloroform, which is de-aerated and refrigerated at 4 °C., is deposited on the functionalized surface of one of the electrodes. A glass slide precoated with a silicone-based formulation (of Petrarch™ Glasselad™ 6C type) is placed on the drop so as to form a homogeneous film. The device is placed in a ventilated oven at 45 °C. for 15 h. The glass slide is then removed and the device is washed several times, alternatively with a 20% solution of acetic acid in methanol and lastly with pure methanol, and is finally dried under a flow of argon. The resonator is inserted into the feedback loop of a variable gain amplifier. The value of the gain necessary to maintain the oscillation and the resonant frequency are measured simultaneously. The assembly constitutes a sensor suited to the detection of atrazine, a commonly-used herbicide.

EXAMPLE 2

A transducer is made up of 2 Love wave delay lines obtained by deposition of comb-type interlocking metal electrodes (vaporized aluminium, 2500 Å thickness, 50 fingers per electrode, 80 λ opening, centre-to-centre distance 125 λ) on an ST quartz substrate, followed by deposition of a layer of silica $SiO_2$ by PECVD. The orientation of the substrate is selected such that the desired mode propagates in the plane YZ, with polarization parallel to the X-axis. The thickness of the layer of silica is 1.48 μm. The wavelength λ is 32 μm. Each delay line is inserted into the feedback loop of a variable gain amplifier fitted with a device for automatic control of the gain by reference to an external reference. The surface of one of these lines is made hydrophilic and then treated with methacryloxypropyltrimethoxysilane in the presence of triethylamine, so as to graft methacrylic groups to the surface. The rest of the transducer is protected with a masking resin, of the type commonly employed in photolithography, during this operation and those which follow, so as to delimit the area to be treated. One drop of a solution identical in composition to that of the above example is deposited on the functionalized area. A glass slide precoated with a silicone-based formulation (of Petrarch™ Glasselad™ 6C type) is placed on the drop as before so as to form a homogeneous film. The rest of the treatment is carried out as in the above example. The manufacture is completed by eliminating the resin which served to protect the areas required to remain bare, according to the usual method of dissolution in hot acetone.

EXAMPLE 3

A device $SD^1$ as represented in FIG. 6 may be produced by means of the sequence of steps described in FIG. 7. The substrates, depicted in FIG. 7 includes two delay lines, which are coated with different materials L and L', at least one of which is a molecular fingerprint material. Interlocking electrodes are associated with each delay line, $SE_1$-$SE_2$ for the delay line containing the material L and $SE_1'$-$SE_2'$ for the delay line containing the material L'. A process for producing this device may be as follows:

The two lines are initially coated with two layers of positive resin R1, R2 for photolithography (Shipley Microposit™ type), separated by a layer M1 of 1000 Å of aluminium deposited by vaporization. The aluminium is laid bare and etched above the first delay line (steps 7a) to 7c)). A second phase of photolithography through the mask thus formed makes it possible to lay bare the substrate at the first delay line (steps 7d and 7e). A layer of material I (molecular fingerprint material, dark trace in the figure) is prepared as in the above example (step 7f). This layer is stripped off by reactive ion etching (RIE) down to the level of the aluminium (step 7g). A new layer of resin R3 is deposited (step 7h), and the entire process is repeated (steps 7i) to 7o)), so as to achieve deposition of the material II (light trace in the figure). The latter may be a material of composition identical to the material I, but crosslinked in the absence of gauge molecule, and therefore having no specific binding sites. It may also be another molecular fingerprint material. Steps i) to o) may be repeated as many times as necessary in order to produce a multi-sensor device. The manufacture is completed by removing the residual layer of resin according to the usual method (dissolution in hot acetone). The aluminium film is also removed during this operation.

I claim:

1. A chemical sensor which is selective for a species G comprising an acoustic wave transducer and a sensitive layer on a surface of an element of the transducer, wherein the sensitive layer comprises a macroporous, crosslinked molecular fingerprint material which has cavities whose steric and functional configuration is specifically suited to capturing species G in the cavities, said sensitive layer and the cavities therein having been prepared by in situ polymerization of polymerizable monomers and crosslinking agents as a uniform film upon said surface.

2. Chemical sensor according to claim 1, wherein the molecular fingerprint material is a highly crosslinked organic polymer obtained by polymerization of a composition comprising one or more monomers that are crosslinkable in the presence of an extractable species G' whose chemical structure is similar or identical to that of species G.

3. Chemical sensor according to claim 2 wherein the species G' are molecules or ions or a combination of molecules and/or ions of given stoichiometry.

4. A chemical sensor which is selective for a species G comprising an acoustic wave transducer and a sensitive layer, wherein the sensitive layer comprises a macroporous, crosslinked molecular fingerprint material which has cavities whose steric and functional configuration is specifically suited to capturing species G in the cavities and wherein the transducer is a volume acoustic wave transducer comprising a piezoelectric material inserted between two electrodes, at least one of the electrodes being coated with the sensitive layer.

5. Chemical sensor according to claim 1, wherein the transducer is a surface wave transducer, comprising a piezoelectric material on which two interlocking series of electrodes are placed, separated by a surface on which is deposited the sensitive layer.

6. A chemical sensor which is selective for a species G comprising an acoustic wave transducer and a sensitive layer, wherein the sensitive layer comprises a macroporous, crosslinked molecular fingerprint material which has cavities whose steric and functional configuration is specifically suited to capturing species G in the cavities and wherein the acoustic wave transducer is a surface wave transducer, comprising a piezoelectric material on which two interlocking series of electrodes are placed, separated by a surface on which is deposited the sensitive layer, the piezoelectric material being a thin film of piezoelectric material, the sensitive layer being deposited at the surface of the film so as to generate acoustic waves of Lamb wave type.

7. A chemical sensor which is selective for a species G comprising an acoustic wave transducer and a sensitive layer, wherein the sensitive layer comprises a macroporous, crosslinked molecular fingerprint material which has cavities whose steric and functional configuration is specifically suited to capturing species G in the cavities and wherein the acoustic wave transducer is a surface wave transducer, comprising a piezoelectric material on which two interlocking series of electrodes are placed, separated by a surface on which is deposited the sensitive layer, and further wherein the transducer comprises an intermediate layer between the sensitive layer and the piezoelectric material, in which the acoustic waves are confined.

8. Chemical sensor according to claim 1 comprising an intermediate layer located between the sensitive layer and the transducer, ensuring the creation of strong chemical interactions between the sensitive layer and the transducer.

9. Chemical sensor according to claim 8, wherein the intermediate layer comprises silanes of general formula $R_nSIX_{n-4}$, with X being a hydrolysable group, R a non-hydrolysable organic group having functions capable of reacting with the monomers used to obtain the crosslinked polymer, the said intermediate layer promoting the adhesion of the sensitive layer to a piezoelectric substrate.

10. A chemical sensor which is selective for a species G comprising an acoustic wave transducer and a sensitive layer wherein the sensitive layer comprises a macroporous, crosslinked molecular fingerprint material which has cavities whose steric and functional configuration is specifically suited to capturing species G in the cavities, the chemical structure further comprising an intermediate layer located between the sensitive layer and the transducer, ensuring the creation of strong chemical interactions between the sensitive layer and the transducer wherein the intermediate layer comprises compounds of RSH or RS-SR' type, with R and R' being non-hydrolysable organic groups having functions capable of reacting with the monomers used to obtain the crosslinked polymer, the said intermediate layer promoting adhesion of the sensitive layer to a metal electrode.

11. A chemical sensor which is selective for a species G comprising an acoustic wave transducer and a sensitive layer wherein the sensitive layer comprises a macroporous, crosslinked molecular fingerprint material which has cavities whose steric and functional configuration is specifically suited to capturing species G in the cavities, wherein the molecular fingerprint material is a highly crosslinked organic polymer obtained by polymerization of a composition comprising one or more monomers that are crosslinkable in the presence of species G' whose chemical structure is similar or identical to that of species G the chemical sensor further comprising a combination of a chemical sensor defined above, and a chemical sensor comprising an acoustic wave transducer and a layer consisting of a highly crosslinked polymer identical to that of the sensitive layer but obtained in the absence of species G'.

12. A process for producing a sensor according to claim 11, comprising the steps of:

the production, through the agency of a first mask which leaves a first area of a substrate free, of a first component of molecular fingerprint material, wherein the substrate allows the propagation of acoustic waves;

the production, through the agency of a second mask which leaves a second area of the substrate free, of a second component of material crosslinked in the absence of a gauge molecule;

the production on either side of the first area and the second area of acoustic wave inducer and/or receptor means.

13. Process for producing a sensor according to claim 11, comprising the following steps:

a) preparation on a substrate which allows the propagation of acoustic waves with an alternation of a first layer of resin for photolithography, of a metal layer and of a second layer of resin for photolithography;

b) elimination of the second layer of resin in a first area;

c) etching of the metal layer in the first area;

d) attack of the first layer of resin in the first area and optionally of the rest of the second layer of resin;

e) exposure of the substrate in the first area during attack of the first layer of resin;

f) preparation, on the substrate in the first area, of a first component made of molecular fingerprint material;

g) preparation of a third layer of resin;

h) elimination of the third layer of resin in a second area;

i) etching of the metal layer in the second area;

j) attack of the first layer of resin in the second area and optionally of the rest of the third layer of resin;

k) exposure of the substrate in the second area during attack of the first layer of resin;

l) preparation, on the substrate in the second area, of a second component made of material crosslinked in the absence of gauge molecule;

m) elimination of the metal layer and of the first layer of resin.

14. Process according to claim 12 wherein the second component is made of material identical in composition to that of the first component, but is polymerized and crosslinked in the absence of a gauge molecule.

15. Process according to claim 13, further comprising producing means for inducing at least one acoustic wave in said first and second areas of the substrate.

16. Process according to claim 15, further comprising production, on either side of the first area and the second area, of acoustic wave inducer/receptor means.

17. Process according to claim 16, further comprising production, on either side of the first area and the second area, of conductive electrodes.

18. Process according to claim 13, wherein the second component is made of material identical in composition to that of the first component, but is polymerized and crosslinked in the absence of a gauge molecule.

* * * * *